United States Patent
Ning et al.

(10) Patent No.: US 10,113,999 B2
(45) Date of Patent: Oct. 30, 2018

(54) METHOD AND A DEVICE FOR DETECTING A SUBSTANCE

(71) Applicant: City University of Hong Kong, Kowloon (HK)

(72) Inventors: Zhi Ning, Kowloon Tong (HK); Ka Lok Chan, Kowloon (HK); Dane Westerdahl, Kowloon (HK); Ka Chun Wong, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 0 days.

(21) Appl. No.: 14/305,189

(22) Filed: Jun. 16, 2014

(65) Prior Publication Data
US 2015/0253297 A1 Sep. 10, 2015

Related U.S. Application Data

(60) Provisional application No. 61/949,562, filed on Mar. 7, 2014.

(51) Int. Cl.
*G01J 5/00* (2006.01)
*G01N 33/00* (2006.01)
*G01N 21/3504* (2014.01)

(52) U.S. Cl.
CPC ....... *G01N 33/004* (2013.01); *G01N 21/3504* (2013.01); *G01N 2201/061* (2013.01); *G01N 2201/068* (2013.01)

(58) Field of Classification Search
CPC ....... G01J 5/34; G01J 5/20; G01J 5/02; H01L 37/02; G08B 13/191

USPC ....................................................... 250/338.3
See application file for complete search history.

(56) References Cited

U.S. PATENT DOCUMENTS

| | | | | |
|---|---|---|---|---|
| 5,283,845 | A * | 2/1994 | Ip ..................................... | 385/24 |
| 5,464,983 | A * | 11/1995 | Wang ............................ | 250/343 |
| 6,428,122 | B1 * | 8/2002 | Henry et al. ...................... | 312/1 |
| 2004/0124348 | A1 * | 7/2004 | Utz et al. ........................ | 250/251 |
| 2006/0017578 | A1 * | 1/2006 | Shubinsky et al. ........... | 340/578 |
| 2007/0152154 | A1 * | 7/2007 | DeCamp ............... | G01J 3/2803 |
| | | | | 250/339.07 |
| 2010/0202734 | A1 * | 8/2010 | DeCorby ........................ | 385/43 |
| 2011/0108720 | A1 * | 5/2011 | Ford et al. ..................... | 250/262 |
| 2012/0287418 | A1 * | 11/2012 | Scherer et al. ................. | 356/51 |

OTHER PUBLICATIONS

Noro et al. "CO2/H2O Gas sensor Using a Tunable Fabry-Perot Filter with Wide Wavelength Range" 2003, IEEE, 319-322.*

(Continued)

*Primary Examiner* — David Porta
*Assistant Examiner* — Mamadou Faye
(74) *Attorney, Agent, or Firm* — Renner Kenner Greive Bobak Taylor & Weber

(57) ABSTRACT

A device for detecting a substance includes a light source arranged to emit a light signal through a sample cell, wherein the sample cell is arranged to temporally house a sample compound having a portion of the substance, and an optical processing module arranged to detect the light signal emitted through the sample cell to identify physical attributes of the light signal altered by the sample compound, wherein the physical attributes of the light signal altered by the sample compound is processed so as to detect the substance within the sample compound.

23 Claims, 13 Drawing Sheets

(56) References Cited

OTHER PUBLICATIONS

Adler et al. "Mid-infrared Fourier transform spectroscopy with a broadband frequency comb" Oct. 11, 2010, Optical Society of America, vol. 18, No. 21, Optics Express, p. 21861-21872.*

Ebermann et al. "Design, Operation and Performance of Fabry-Perot-Based MWIR Microspectrometer", Sensor + Test Conference 2009-IRS2 Proceedings, p. 233-238.*

Deutscher et al. "A Fourier transform infrared trace gas analyser for atmospheric applications" Copernicus Publications on behalf of the European Geosciences Union, ResearchGate, May 2012, p. 3717-3769.*

Drossart et al. "VIRTIS-H: a high spectral resolution channel for the Rosetta Infrared Imaging Spectrometer" Proceedings of SPIE vol. 4131, 2000, pb.78-87.*

\* cited by examiner

METHOD AND A DEVICE FOR DETECTING A SUBSTANCE

TECHNICAL FIELD

The present invention relates to a device and a method for detecting a substance and particularly, although not exclusively, to a device and a method for dispersive infrared spectroscopy measurements of greenhouse gas using a Fabry-Pérot interferometer sensor.

BACKGROUND

Carbon dioxide ($CO_2$) is one of the most important greenhouse gas in the atmosphere with serious impacts on radiative warming the planet earth. Atmospheric $CO_2$ dissolved in water is known to cause ocean acidification harming aquatic life forms. The global atmospheric background concentration has increased slowly but steadily at a rate of 1.95 ppmv per year in the last century as measured at the National Oceanic and Atmospheric Administration (NOAA) Mauna Loa Observatory, reaching a level of 400 ppmv in May 2013. The rising atmospheric $CO_2$ concentration has motivated many nations to regulate carbon emissions.

Accurate measurements of atmospheric $CO_2$ are important not only to provide an objective basis for the emission report verification at regional to continental scales, to improve the understanding of the sources and sinks of $CO_2$ in complex urban terrain, but also to investigate their temporal and spatial distribution as well as their transportation. In order to improve the estimation of regional $CO_2$ distribution for transport model flux inversion calculations, expansion of $CO_2$ monitoring networks to improve the spatial coverage is necessary and the development of sensitive and reliable $CO_2$ analyzer for monitoring purpose is required.

SUMMARY

In accordance with a first aspect of the present invention, there is provided a device for detecting a substance comprising: a light source arranged to emit a light signal through a sample cell, wherein the sample cell is arranged to temporally house a sample compound having a portion of the substance; and an optical processing module arranged to detect the light signal emitted through the sample cell to identify physical attributes of the light signal altered by the sample compound, wherein the physical attributes of the light signal altered by the sample compound is processed so as to detect the substance within the sample compound.

In an embodiment of the first aspect, the sample compound includes a gas.

In an embodiment of the first aspect, the optical processing comprises a light sensor.

In an embodiment of the first aspect, the light sensor includes a pyroelectric sensor.

In an embodiment of the first aspect, the light sensor further includes a Fabry-Pérot interferometer.

In an embodiment of the first aspect, the pyroelectric sensor is integrated with the Febry-Pérot interferometer.

In an embodiment of the first aspect, the light sensor is a Fabry-Pérot interferometer sensor.

In an embodiment of the first aspect, the light signal is at least partially absorbed by the substance in the sample cell.

In an embodiment of the first aspect, the physical attributes include a signal strength of the light signal at one or more wavelengths emitted by the light source.

In an embodiment of the first aspect, the physical attributes include an optical spectrum of the light signal emitted by the light source.

In an embodiment of the first aspect, the light source is a broad band infrared light source.

In an embodiment of the first aspect, the light signal is in a range of wavelengths between 3 μm to 5 μm.

In an embodiment of the first aspect, the optical processing module further comprises a micro-electro-mechanical-system arranged to enable the optical processing module to detect the signal strength of the light signal at one or more wavelengths.

In an embodiment of the first aspect, the optical processing module further comprises a photo detector and two layers of glass separated by a variable distance controlled by a variable electrical signal.

In an embodiment of the first aspect, the sample cell is a gas cell arranged to connect with a gas flow system for flowing the gas into and out of the gas cell.

In an embodiment of the first aspect, the air flow system comprises an HEPA filter at an inlet of the gas cell for blocking aerosol from entering the gas cell.

In an embodiment of the first aspect, the substance includes a greenhouse gas.

In an embodiment of the first aspect, the substance includes at least one of carbon dioxide, methane, nitrous oxide or water.

In accordance with a second aspect of the present invention, there is provided a method for detecting a substance comprising the steps of: temporally housing a sample compound having a portion of the substance; emitting a light signal through the sample compound; detecting the light signal emitted through the sample cell; and processing the detected light signal; wherein physical attributes of the light signal altered by the sample compound is identified and processed so as to detect the substance within the sample compound.

In an embodiment of the second aspect, the light signal is detected by a Fabry-Pérot interferometer sensor.

In an embodiment of the second aspect, the light signal is at least partially absorbed by the temporally housed substance.

In an embodiment of the second aspect, the physical attribute includes a signal strength of the light signal emitted at one or more wavelengths.

In an embodiment of the second aspect, the physical attribute includes an optical spectrum of the emitted light signal.

In an embodiment of the second aspect, the light source is emitted by a broad band infrared light source.

In an embodiment of the second aspect, further comprises the step of: manipulating a micro-electro-mechanical-system arranged to enable the signal strength of the light signal at one or more wavelengths to be detected.

In an embodiment of the second aspect, the sample compound includes a gas, and is temporally housed in a gas cell arranged to connect with an air flow system for flowing the gas into and out of the gas cell.

In an embodiment of the second aspect, the substance includes a greenhouse gas.

BRIEF DESCRIPTION OF THE DRAWINGS

Embodiments of the present invention will now be described, by way of example, with reference to the accompanying drawings in which.

DETAILED DESCRIPTION OF THE INVENTION

The inventors have, through their own research, trials and experiments, devised that, various $CO_2$ sensors and monitors have been developed with a wide range of cost, sensitivity and stability. The measuring principles can be divided in two major categories: First, chemical gas sensors such as mixed oxide capacitors, and solid electrolytes, featuring low energy consumption and compact size but short lifetime and low durability. Second, light absorption based approaches, such as non-dispersive infrared (NDIR), Fourier Transform Infrared (FTIR) and spectrum based Cavity Ring-Down Spectroscopy (CRDS) etc. NDIR is a common technique for atmospheric $CO_2$ measurement due to its higher accuracy and durability than chemical cells, and much lower cost than CRDS. However, the NDIR measurement technique still strongly depends on the influence of other infrared absorbing gases. Frequent calibration and correction of interference from other gases are necessary in order to obtain an accurate measurement. Moreover, non-linear absorption is often an issue for infrared spectroscopic measurement. Correcting those effects require measurement at reference wavelength channels and complicated calibration and correction functions.

In this invention, an embodiment of an absorption spectrum based approach of atmospheric CO2 measurement using a scanning Fabry-Pérot interferometer (FPI) sensor with continuous dispersive infrared spectral analysis is disclosed, including an evaluation of this spectral fitting technique regarding accuracy and interference from other infrared absorbing gases, such as CO and water vapor. An iterative retrieval algorithm was developed and validated for non-linear absorption corrections. Modelled data and comparison measurements were used to examine the performance of the retrieval. In some example embodiments, the developed DIRS system and retrieval algorithm feature auto-correction for both non-linear effect of absorption and interference from other co-existing infrared absorbers. Both effects have been the major limitations of greenhouse gas measurements, for example in most widely used NDIR greenhouse gas measurement. By using a micro electro mechanical system (MEMS) of FPI sensor, the physical size and cost of the system may be greatly reduced by the newly developed retrieval algorithm for easy field deployment. In addition, this measurement technique is not limited to CO2 measurement by simultaneously including other infrared absorbing gas measurements, e.g. CH4, CO, N2O etc., which makes it an advantageous option for applications of atmospheric gas monitoring and indoor air quality measurements.

Figure 1A:
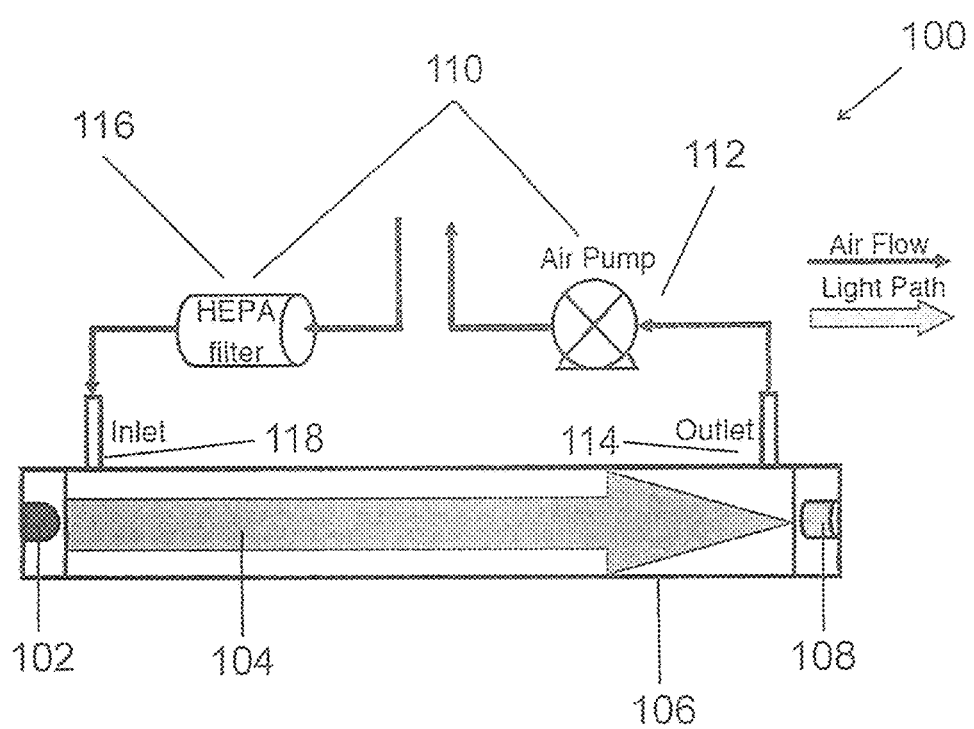
FIG. 1A is a schematic diagram of the device for detecting a gas in accordance with an embodiment of the present invention.

Referring to FIG. 1A, there is provided an embodiment of a device 100 for detecting a substance comprising: a light source 102 arranged to emit a light signal 104 through a sample cell 106, wherein the sample cell 106 is arranged to temporally house a sample compound having a portion of the substance; and an optical processing module 108 arranged to detect the light signal 104 emitted through the sample cell 106 to identify physical attributes of the light signal 104 altered by the sample compound, wherein the physical attributes of the light signal 104 altered by the sample compound is processed so as to detect the substance within the sample compound.

In this embodiment, sample compound such as sample gas may be injected to a sample cell or a gas cell 106, such that the gas is at least temporally contained in the gas cell 106. A gas flow system 110 such as an air pump 112 connected to an outlet 114 of the gas cell 106 for flowing the gas into and out of the gas cell 106. Light source 102 is provided at one end of the sample cell 106 for emitting a light signal 104 through the sample cell 106. An optical processing module 108 is provided at the other end of the sample cell 106 for detecting the light signal 104 emitted through the sample cell 106.

When the light signal 104 is transmitted through the sample gas housed in the gas cell 106, the light signal 104 is at least partially absorbed by the substance in the sample cell 106. The substance may include greenhouse gases such as carbon dioxide which absorb electromagnetic wave with a wavelength of around 4280 nm in the range of 3 μm to 5 μm, and different substances have different absorption spectrums in the detected range. As a result, the optical spectrum of the emitted light signal 104 is altered by the sample compound and is detected by the optical processing module 108 or the light sensor included in the optical processing module 108. The optical processing module 108 may then compare the difference between the emitted and the detected light signal 104 to determine the existence or the amount of substance included in the sample compound housed in the sample cell 106 according to the variance of the difference obtained.

Figure 1B:
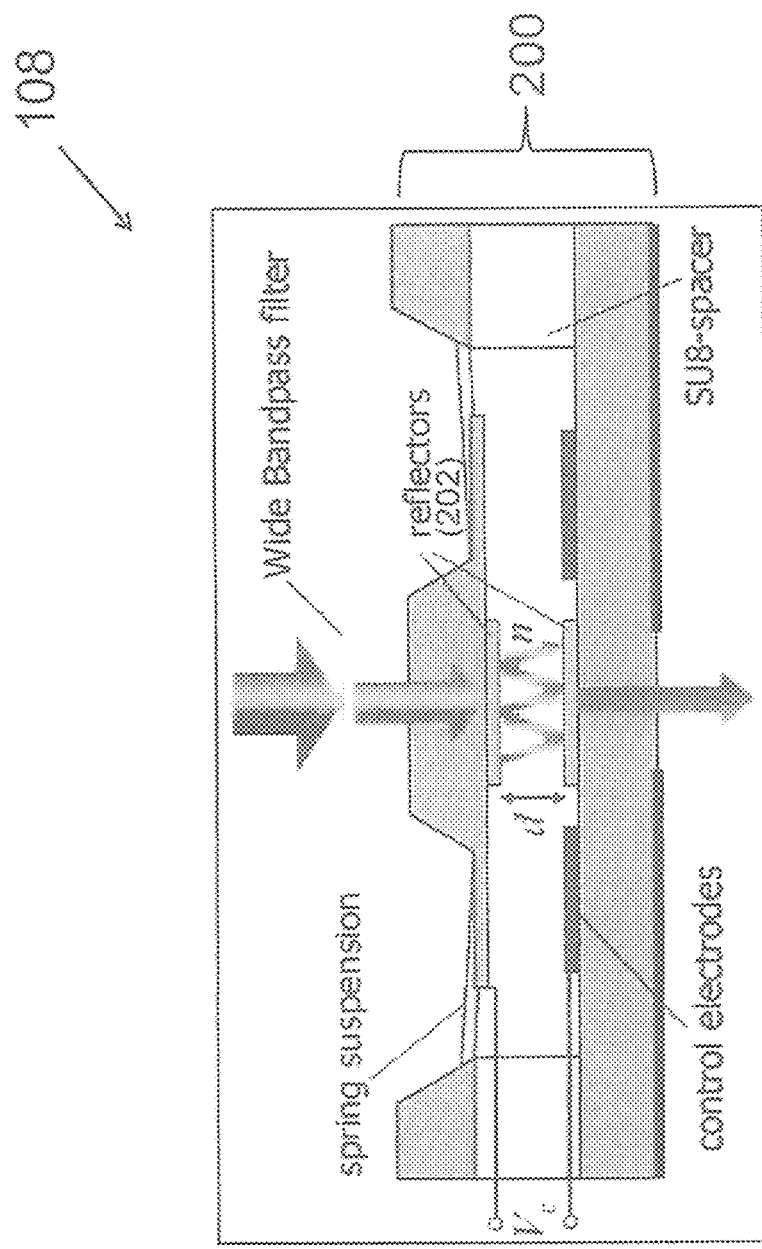
FIG. 1B is a schematic diagram of an FPI sensor in the device of FIG. 1A.

Preferably, the optical processing module further comprises a micro-electro-mechanical-system (MEMS) arranged to enable the optical processing module 108 to detect the signal strength of the light signal at one or more wavelengths. As shown in FIG. 1B, the MEMS 200 in the optical processing module 108 may be controlled by a external control voltage $V_C$ such that the distance between the reflectors 202 increase or decrease, and the wavelength detected by the light sensor in the optical processing module may be controlled accordingly.

In an example embodiment, the device 100 for detecting a substance consist of a broad band infrared light source 102 (MIRL-17-900, Intex, Inc.), a pyroelectric sensor integrated with the Fabry-Pérot interferometer (FPI, LFP-3950L-337, InfraTec GmbH), an aluminum sampling gas cell 106 with surface anodized in black color and an air flow system 110. The infrared source 102 is placed at one end of the sampling gas cell 106 while the FPI sensor 108 is placed at the other end of the gas cell 106, resulting in an optical absorption path of 28 cm. The power of the infrared light source 102 was 680 mW. The FPI sensor 108 scans in the wavelength range of 3900 nm to 5220 nm with 20 nm step (67 channels in total) with full width half maximum (FWHM) spectral resolution of 78.8 nm at the $CO_2$ absorption band (~4280 nm). The temporal resolution of the instrument 100 is about 9 s including 8 s scanning time and 1 s relaxation time. Air flow of the system 110 is achieved by a DC vacuum pump 112 positioned on the outlet side 114 of the sampling cell 106. Ambient air is pumped into the sampling gas cell 106 through Teflon tubings for analysis. Optionally, a high efficiency particulate air (HEPA) filter 116 may be included in the air flow system 110, and is placed in front of the inlet 118 of the sampling cell 106 to remove aerosol in the ambient air to avoid aerosol entering the sampling cell 106 affecting the optical path by scattering and contamination of the optical window of both the infrared light source 102 and the FPI sensor 108. Light carrying physical attributes such as wavelengths and optical spectrum of the light signal 104, and also absorption information of the ambient air is recorded by the FPI sensor 108 for further spectral analysis. In this example, a 28 cm cylinder aluminum sample cell 106 with an inner diameter of 1 cm was used, resulting in a sampling volume of 22 cm$^3$. The sampling air flow rate is set to 0.5 liter per minute (lpm). Alternatively, sample cells with different volume, and different sampling air flow rate may be used. The voltage signal representing the light intensity during the scan is acquired by a micro electronic board and converted to a digital signal which is recorded by a computing device.

In order to measure the lamp spectrum of the light source 102, the sampling cell 106 was filled with zero air (21% oxygen ($O_2$), 79% nitrogen ($N_2$), $CO_2 \le 2$ ppmv). The dark spectrum was measured by turning off the infrared light source 102. Both spectra were averaged over 100 scans in order to minimize the noise level for further processing. During the entire experiment period, the lamp and dark spectra were checked regularly and did not show any significant drift (less than 0.5%). In one example embodiment, all the measured absorption spectra were corrected by subtracting the dark spectrum, followed by the division by the reference lamp spectrum. Subsequently, the logarithm is taken to convert the data to optical density. Reference absorption cross section for $CO_2$, $CO$ and $H_2O$ was then fitted to the spectra. The high resolution cross sections are first convoluted with the instrument spectral resolution function provided by the manufacturer (InfraTec GmbH, Germany). A second order polynomial is included in the fit between the measured and reference absorption spectra of the gases to adjust for additional light attenuation, e.g., intensity fluctuation of the light source 102, sensitivity decay of the sensor 108, etc. In order to correct for small uncertainties in the wavelength mapping, a small shift of wavelength (±5 nm) is tolerated during the fitting process. A Levenberg-Marquardt algorithm with cubic spline interpolation for the spectrum interpolation is employed for the non-linear optimization of the spectral fitting. The spectral fit is applied to the wavelength range from 4000 nm to 5000 nm covering a strong $CO_2$ absorption band.

Figure 2:
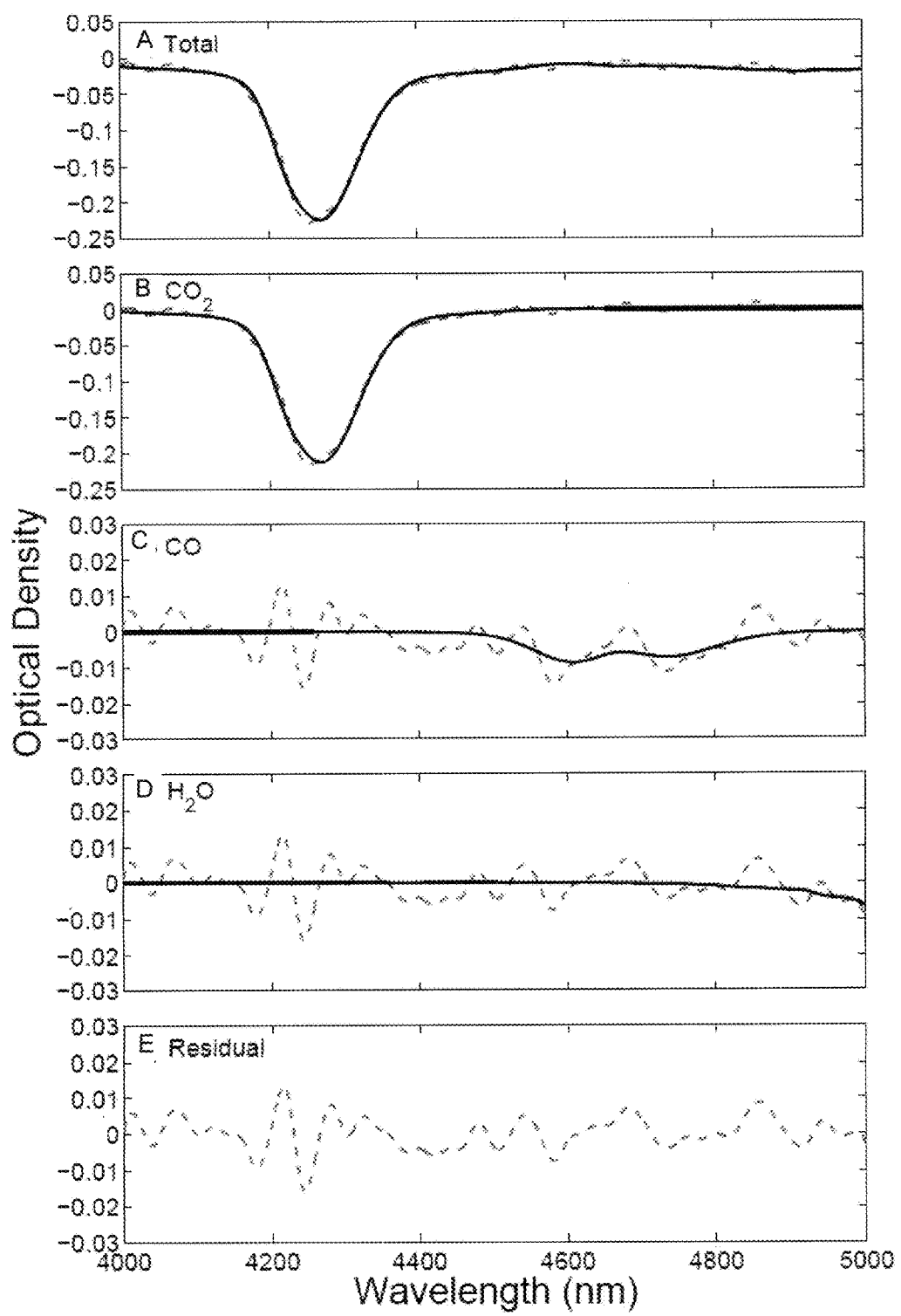
FIG. 2A is a plot of an example of a $CO_2$ retrieval using the device in FIG. 1A shown for all absorptions.
FIG. 2B is a plot of an example of a $CO_2$ retrieval using the device in FIG. 1A shown for $CO_2$.
FIG. 2C is a plot of an example of a $CO_2$ retrieval using the device in FIG. 1A shown for CO.
FIG. 2D is a plot of an example of a $CO_2$ retrieval using the device in FIG. 1A shown for $H_2O$.
FIG. 2E is a plot of an example of a $CO_2$ retrieval using the device in FIG. 1A showing the residual of the fit.

An example spectral fit is shown in FIG. 2. Since the lamp spectrum is assumed to be free of $CO_2$ absorption, the resulting fitting coefficients are directly treated as the slant column densities of individual gases. An iterative algorithm is employed for the non-linear absorption correction, details of the iterative algorithm are presented in the later part of this disclosure. The measured slant column densities are converted to mixing ratios by dividing the optical path length by the air density, which was calculated based on the pressure and temperature of the sampling air. The measurement error is estimated following a standard approach as known by a person skilled in the art. The detection limit is defined as 2 times the measurement error.

In FIG. 2, the spectrum was taken with $CO_2$ mixing ratio of (423.2±6.3) ppmv. Fitting of the absorption cross sections (red curves) and the measured optical densities (blue curves) are shown for all absorptions (FIG. 2A), $CO_2$ (FIG. 2B), $CO$ (FIG. 2C) and $H_2O$ (FIG. 2D). FIG. 2E shows the residual of the fit. 10 cm.

Preferably, the measurement of light absorption is not directly proportional to the amount of gas molecules in the optical path, especially at high gas concentrations. This effect is mainly due to the low spectral resolution of instrument spectrograph that is not able to fully reproduce the absorption signal: most of the gas molecules have highly resolved rotational absorption patterns in the infrared spectral range and the optical densities of the absorption lines of those molecules are usually very high. Measuring those absorption lines with a low spectral resolving instrument is less sensitive to the variation of absorption compared to that with high resolution, which results in a non-linear response of the measured absorption to the number of gas molecules in the optical path.

In order to quantify this effect, the inventors have performed a simulation study to investigate the degree of non-linearity of light absorption. Light intensity measured by an instrument after passing through a volume of absorbing matter can be described by the Lambert-Beer law.

$$I(\lambda) = \left[ I_0(\lambda) \cdot \exp\left( -L \sum_i \sigma_i(\lambda) \cdot c_i \right) \right] * F(\lambda') \quad (1)$$

with I being the intensity of the initial light $I_0$ after passing through absorbing matter of distance L, concentrations $c_i$ and absorption cross sections $\sigma_i$ of the different absorbing gases. The convolution (written as operator * in the equation) with the instrument function F represents the influence of the instrument on the spectra including the sampling process. In practice, since the light source spectrum is usually measured using the same spectrometer and therefore the actual spectrum before convolution with the instrument function is unknown, Eq. (1) is not applicable for data retrieval. In normal applications, the problem can be linearized by assuming the optical densities of the gases to be low. In addition, the lamp spectrum has to be smooth and the spectral resolution of the instrument has to be sufficient to reproduce the absorption signal in order to swap the operation of the exponential and the convolution to implement for data retrieval. However, those assumptions are not valid for high optical densities and low spectral resolution measurements. An alternative solution is to model the absorption process stated in Eq. (1). In order to estimate the non-linearity, the absorption optical density of $CO_2$ at 4034 nm measured by high and low spectral resolution spectrograph is calculated. The absorption optical density of $CO_2$ is calculated by simulating the whole absorption process shown in Eq. (2) using literature high resolution absorption cross section.

$$D(\lambda) = -\ln \frac{I_0(\lambda) \cdot \exp(-L \sum \sigma_i(\lambda) \cdot c_i) * F(\lambda')}{I_0(\lambda) * F(\lambda')}. \quad (2)$$

Figure 3:
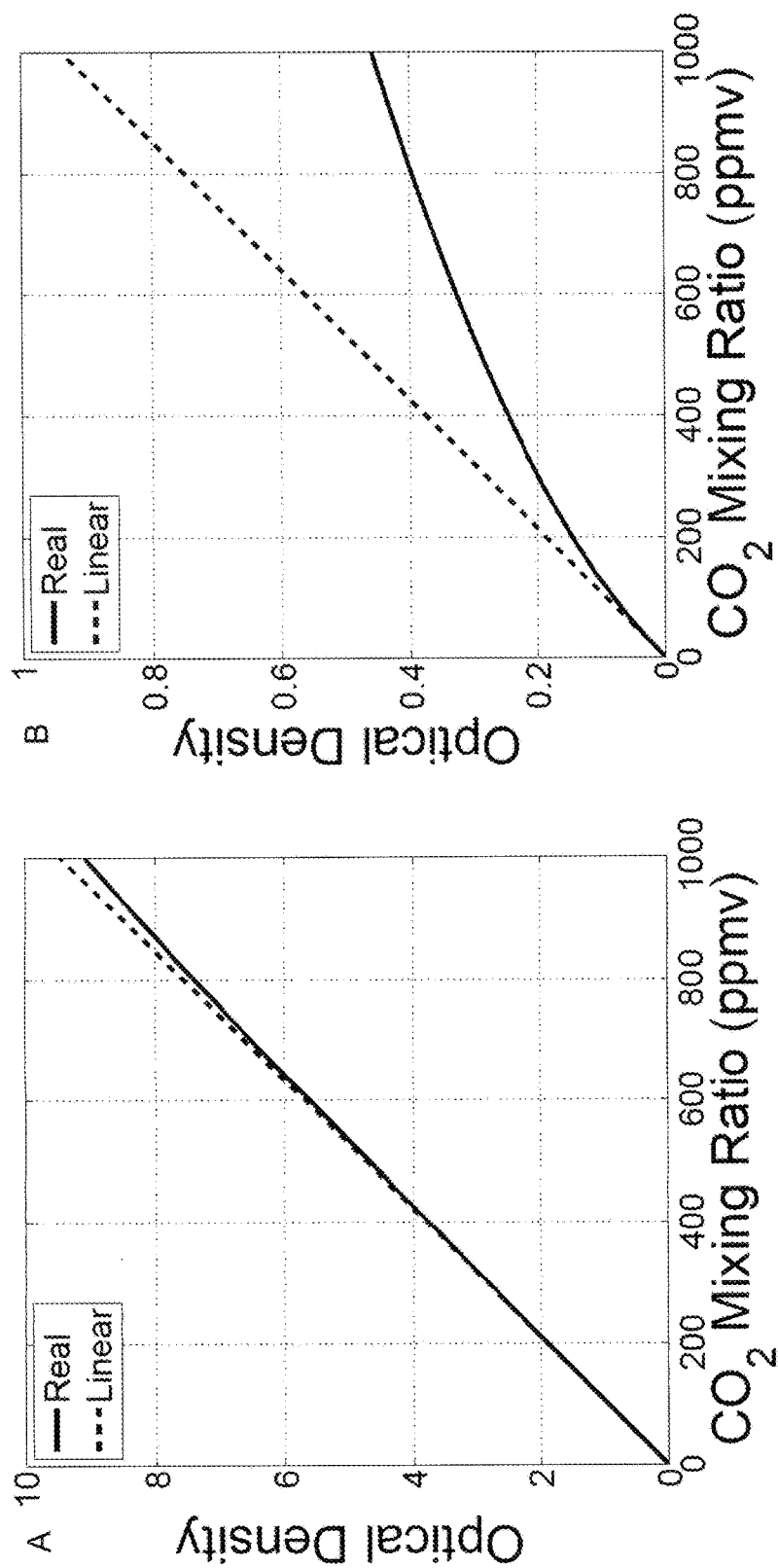
FIG. 3A is a plot of an estimation of $CO_2$ absorption optical density at 4034 nm measured by a high spectral resolution (0.1 nm FWHM) spectrograph.
FIG. 3B is a plot of an estimation of $CO_2$ absorption optical density at 4034 nm measured by a low spectral resolution (78.8 nm FWHM) spectrograph using the device in FIG. 1A.

Referring to FIG. 3, there is shown the simulation results of $CO_2$ absorption optical densities measured by a spectrograph with different spectral resolutions of 0.1 nm (FWHM) (FIG. 3A) and 78.8 nm (FWHM)(FIG. 3B). The simulation was done using a high resolution absorption cross section of $CO_2$. Gaussian shaped instrument functions were used in the simulation. The optical path length is set to 28 cm, and normal atmospheric conditions at room temperature (20° C.) and pressure (1013 hPa). The absorption optical densities D were calculated at each wavelength before convoluting with the instrument function.

The simulation results show that the $CO_2$ absorption optical densities measured by a spectrograph with high spectral resolution are relatively proportional to the number of $CO_2$ molecules in the optical path with difference less than 5% in the range of 0-1000 ppmv. On the other hand, measuring the $CO_2$ absorption optical densities by using a spectrograph with low spectral resolution would result in a large deviation (more than 100%) at 1000 ppmv from the linear case.

Standard non-dispersive infrared measurement techniques employ a look-up calibration table to correct for the non-linear effect. However, there are multiple gases absorbing in the infrared wavelength band and these may interfere with each other. For non-dispersive infrared measurements, cross interference corrections are in most cases necessary. Correcting the non-linear effects and cross interference involves complicated calibration functions. Moreover, the calibration function is only valid in a specified measurement range. Alternatively, in the current approach with multiple wavelength absorption information from the FPI sensor, the non-linear effect can be corrected by using an iterative retrieval algorithm with major influencing gases included in the fit. The absorption cross sections can be modified according to the gas mixing ratios in Eq. (3). The modified absorption cross sections $\sigma_{i,n}$ are used in the fit. The fit result (slant column densities/mixing ratios) is then used to further modify the absorption cross sections.

$$\sigma_{i,n+1}(\lambda) = \frac{-\ln(\exp(-L \cdot \sigma_{i,n}(\lambda) \cdot c_{i,n}) * F(\lambda'))}{L \cdot c_{i,n}}. \quad (3)$$

In the procedure, the loop proceeds until the change in one iteration is less than half of the estimated error of the fit or until the number of iteration reaches 100. The initial estimate can be any non-zero positive real number. The only infeasible initial concentration input is zero, as there will be several vanishing singular values in the singular value decomposition during computing the pseudo inverse of the linear equations. A reasonable initial estimate of the gas mixing ratios as an input of the retrieval can avoid unnecessary calculations. More iteration steps are expected if the difference between the initial estimate and the final retrieved result is large. For example, a reasonable initial estimate of $CO_2$ mixing ratio for ambient measurements is about 400 ppmv. In the measurement routine, the initial estimate of the $CO_2$ mixing ratio is set to the last valid measurement value as the atmospheric $CO_2$ level is expected to be varying slowly. If it is the first measurement, the initial estimate is then set to 400 ppmv. For other applications, e.g., stack emission measurements, in which the $CO_2$ concentration varies in a wide range, more iteration steps as well as processing time for retrieving the data are expected.

Monte Carlo simulations were employed to estimate the influence of different error sources and parameterization of the retrieval on the measurement result. The effect of instrument noise on the retrieval result is estimated numerically through Monte Carlo simulations. The retrieval was applied to simulated absorption spectra with different $CO_2$ mixing ratios and noise levels to estimate how instrument noise could affect the solutions of the retrieval algorithm. A sensitivity study was performed to estimate the effect of the uncertainty of the instrument function on the retrieval results. Detailed results from the model simulation are presented in the later part of this disclosure.

The measurement results from the dispersive infrared instrument were validated by using a series of known concentration standard $CO_2$ gases (21% oxygen ($O_2$), 79% nitrogen ($N_2$), $CO_2 \leq 2$ ppmv). Ten concentration points were used spanning from 100 to 1000 ppmv supplied by a gas distribution system and compared to the retrieved $CO_2$ concentration using our retrieval algorithm. In addition to the laboratory validation, the performance of the dispersive infrared spectroscopy instrument was evaluated in the field for ambient measurement by comparing side by side with a commercial non-dispersive infrared $CO_2$ analyzer (Vaisala GMP343, Vaisala, Finland). The field experiment was conducted at an urban ambient site in Kowloon Tong (22.333° N, 114.170° E), located about 1.5 km north of Mongkok, one of the busiest commercial districts in Hong Kong, and 1 km from the ambient air quality monitoring station (Hong Kong Environmental Protection Department) in Sham Shui Po. The test was carried out continuously from 12 Apr. 2013 to 11 May 2013. Based on the one-month in-situ measurements, a backward trajectory model was employed to investigate an observed $CO_2$ episode in April 2013. Mean diurnal cycle of atmospheric $CO_2$ from analyzing the one month data set is also presented in the later part of this disclosure.

The retrieval is applied to the simulated absorption spectra with different $CO_2$ mixing ratios and noise levels to estimate how instrument noise could affect the solutions of the retrieval algorithm. Normally distributed random noise with standard deviations of 10%, 5% and 1% of the absorption signal are added to the simulated absorption spectra. In order to make the simulation more realistic for urban ambient measurement, typical carbon monoxide (CO) mixing ratios of 2 ppmv and 30,000 ppmv of water vapor (H2O) (equivalent to ambient air at temperature of 30° C., relative humidity of 82% at a pressure of 1013 hPa) are included in all the simulated absorption spectra. The initial $CO_2$, CO and $H_2O$ mixing ratios of the retrieval are set to 400 ppmv, 10 ppmv and 30,000 ppmv, respectively.

Figure 4:
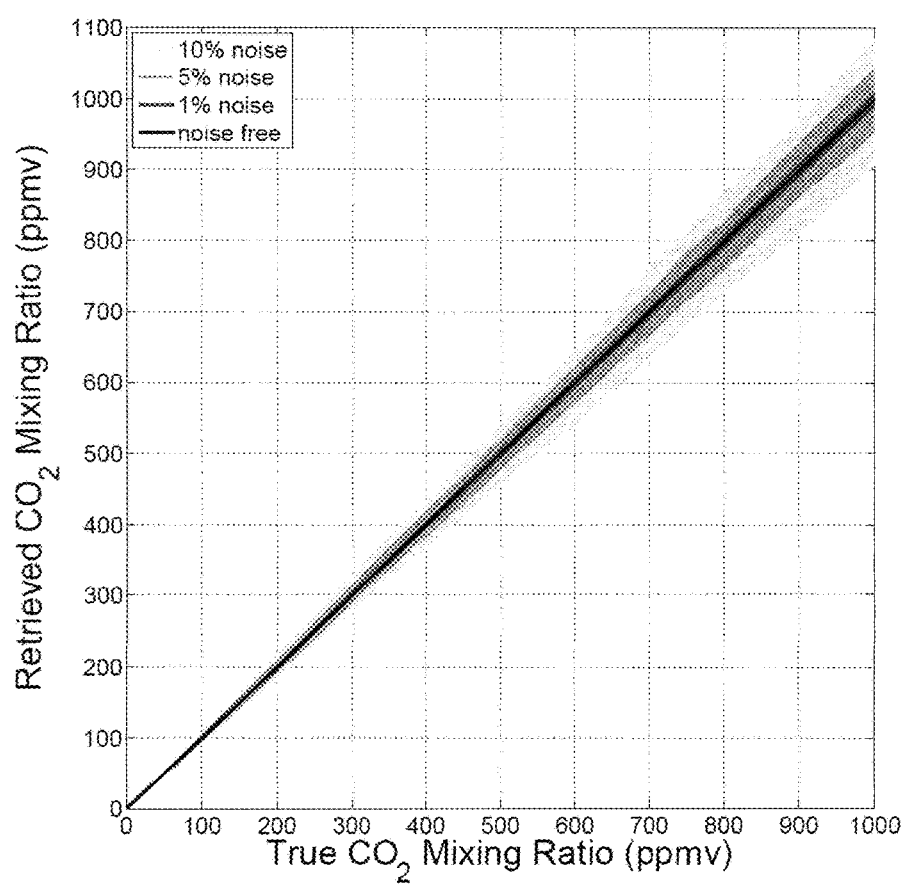
FIG. 4 is a plot of averaged $CO_2$ mixing ratios retrieved from simulated spectra with different $CO_2$ mixing ratios and noise levels.

FIG. 4 shows the mean $CO_2$ mixing ratio retrieved from simulated spectra with different $CO_2$ mixing ratios and noise levels. In this study, 500 Monte Carlo simulations were performed for each $CO_2$ mixing ratio and noise level. Without measurement errors, the retrieval algorithm can exactly reproduce the input $CO_2$ value. Averages of the retrieved $CO_2$ values with different noise levels also agree with the input $CO_2$ values. In general, the standard deviation of the measurement increases with increasing measurement noise. The standard deviation of retrieved $CO_2$ measurement is about 7% for 10% of instrument noise. The measurement errors are considerably smaller than the noise level. In contrast, the measurement error of a single wavelength measurement is the same as the noise level. In addition, the single wavelength channel measurement as in NDIR is not capable of correcting for interference from other absorbers. We performed a comparative evaluation of the performance with NDIR measurements taking typical absorption wavelength of 4280 nm and FWHM of 78.8 nm at the same input as 400 ppmv of $CO_2$, 30,000 ppmv of H2O, and 2 ppmv of CO. The contribution of $H_2O$ and CO in the total absorption is about 2%, equivalent to 8 ppmv of $CO_2$. These two combined effects of gas absorbing interference and larger instrumentation noise caused about 3 times larger error in the determination of ambient $CO_2$ concentrations, which are about 5.5 ppmv for DIRS and 16 ppmv for NDIR for $CO_2$ measurement in our setup. This illustrated that taking multiple wavelengths into account in the retrieval could considerably reduce the measurement errors. Furthermore, increasing the spectral sampling resolution can reduce the error induced by instrument noise.

In addition to CO and $H_2O$, some other infrared absorbers in the atmosphere might also have an effect on the $CO_2$ determination. In order to quantify this effect, a model study is performed by including atmospheric level of methane ($CH_4$, 2 ppmv) and nitrous oxide ($N_2O$, 0.5 ppmv) in the calculation, in which $CH_4$ and $N_2O$ are the fourth and fifth strongest absorbing species in the measured wavelength range present in the atmosphere following $CO_2$, CO and water vapor. The simulated data is retrieved by two scenarios, scenario 1: with including $CH_4$ and $N_2O$ cross section in the retrieval and scenario 2: without including $CH_4$ and $N_2O$ cross sections in the retrieval. Results show retrieval scenario 1 insert space can exactly retrieve the original $CO_2$ concentration and retrieval scenario 2 will result in an error of ~0.2 ppmv for $CO_2$, which is negligible compared to the instrument noise. This result indicated that there is no significant interference caused by $CH_4$ and $N_2O$ in the ambient $CO_2$ determination. In our practice, only interferences from $H_2O$ and CO were considered in the ambient $CO_2$ determination, as $CH_4$ and $N_2O$ caused only negligible impact. For different kinds of measurement in which higher levels of $CH_4$, $N_2O$ or other infrared absorbing species are expected, data retrieval scenario can easily be changed by including the absorption cross sections in the retrieval to correct for the interference.

Figure 5:
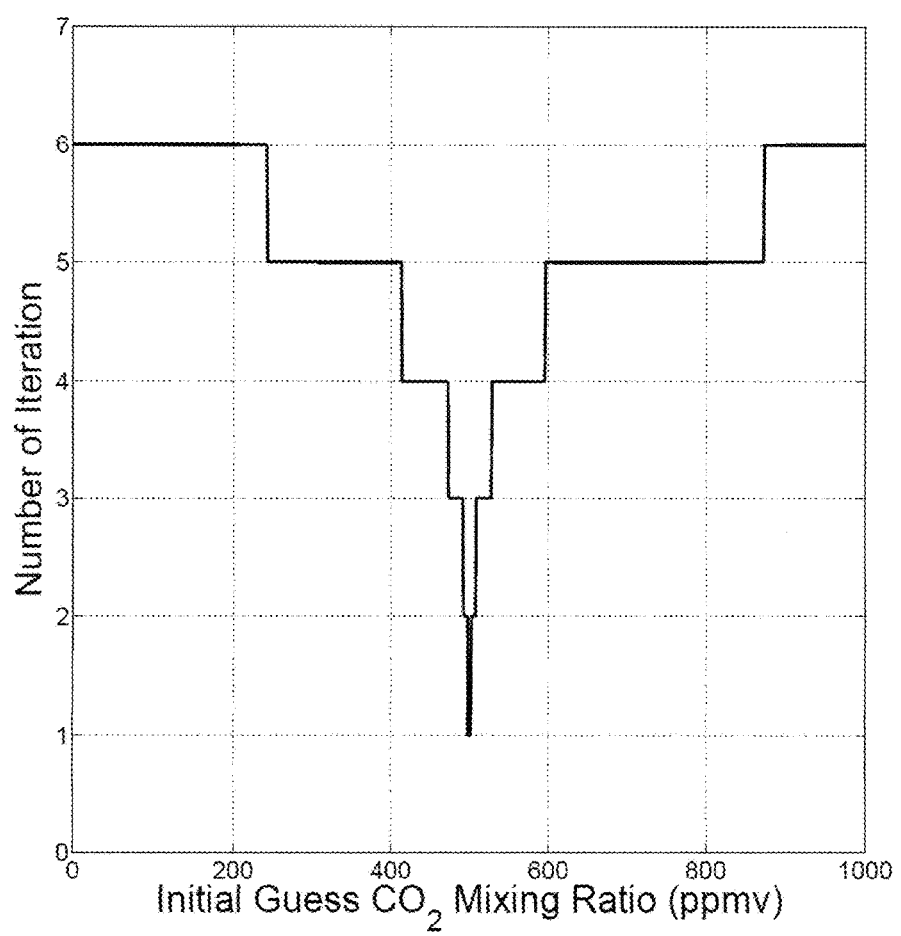
FIG. 5 is a plot showing a number of iteration of the retrieval algorithm in retrieving an absorption spectrum with $CO_2$, CO and $H_2O$ mixing ratios of 500 ppmv, 2 ppmv and 30,000 ppmv in accordance with an embodiment of the present invention.

In the retrieval, initial estimates of the mixing ratios for inputs are required. Reasonable initial estimates could significantly reduce the number of iteration of the retrieval as well as processing time. With reference to FIG. 5, there is shown the number of iterations of the retrieval algorithm in retrieving an absorption spectrum with $CO_2$, CO and $H_2O$ mixing ratios of 500 ppmv, 2 ppmv and 30,000 ppmv, respectively. Normally distributed random noise with standard deviation of 1% of the absorption signal is added to the simulated absorption spectrum. The retrieval started with different initial estimates of $CO_2$ mixing ratio. All the retrieval results show good agreement with the actual value with less than 1 ppmv difference. The 1 σ standard deviation of all the retrieval results is 0.43 ppmv. The result shows that the number of iteration is reduced when the initial estimate is closer to the actual value. However, even with a 500 ppmv difference between the initial estimate and actual values, the number of iterations only increased to six and the algorithm is able to process the calculation while taking the spectrum in the 9 s measurement cycle.

The instrument function, defined as the influence of the instrument on the spectra introduced during the sampling process, has a significant impact on the retrieval of the dispersive infrared measurement. To quantify the uncertainty of this effect, instrument functions with different FWHM are used to retrieve simulated absorption spectra. The simulated absorption spectra are constructed by using a Gaussian shaped instrument function with FWHM of 78.8 nm. Error free conditions are assumed in the simulation. The FWHM of the instrument function used in the retrieval was set to vary from 68.8 nm to 88.8 nm with a 2 nm step. The retrieval is then applied to the simulated absorption spectra with different $CO_2$ concentrations. The initial estimate of $CO_2$, CO and $H_2O$ mixing ratios of the retrieval are set to 400 ppmv, 10 ppmv and 30,000 ppmv, respectively.

Figure 6:
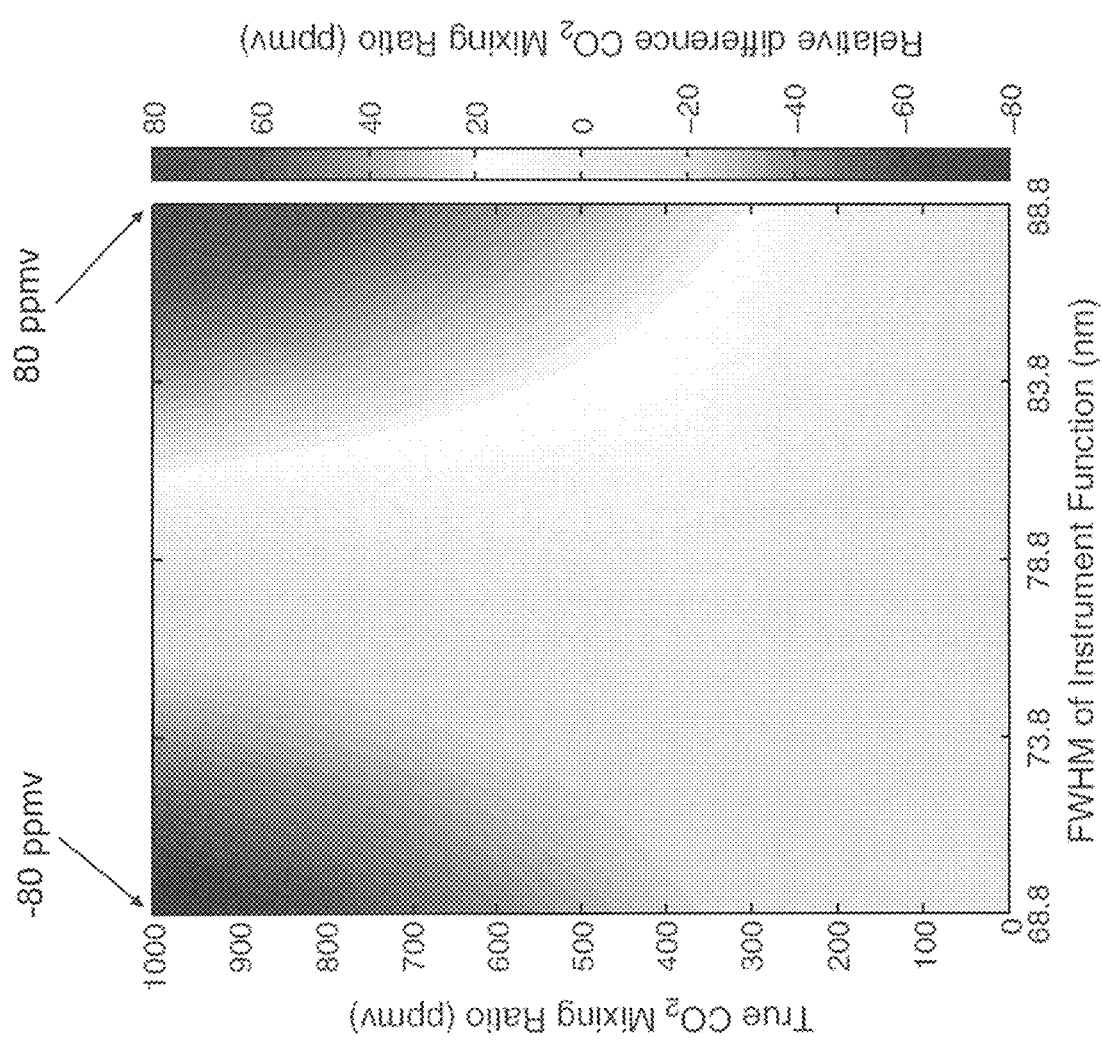
FIG. 6 is a diagram showing a difference between retrieved and input $CO_2$ mixing ratio using different instrument functions.

Referring to FIG. 6, there is shown the retrieval results. The results show that the $CO_2$ levels are overestimated when the FWHM of the instrument function is overestimated. On the other hand, the $CO_2$ levels are under-estimated when the FWHM of the instrument function is under-estimated. Under or over estimating the FWHM of the instrument function with 10 nm can easily induce bias up to 8% to the measurement results. The effect is more significant when the absorption signal goes higher, which indicates that this technique applies only if the instrument function is precisely determined, otherwise extra calibrations of the instrument will be necessary.

Figure 7:
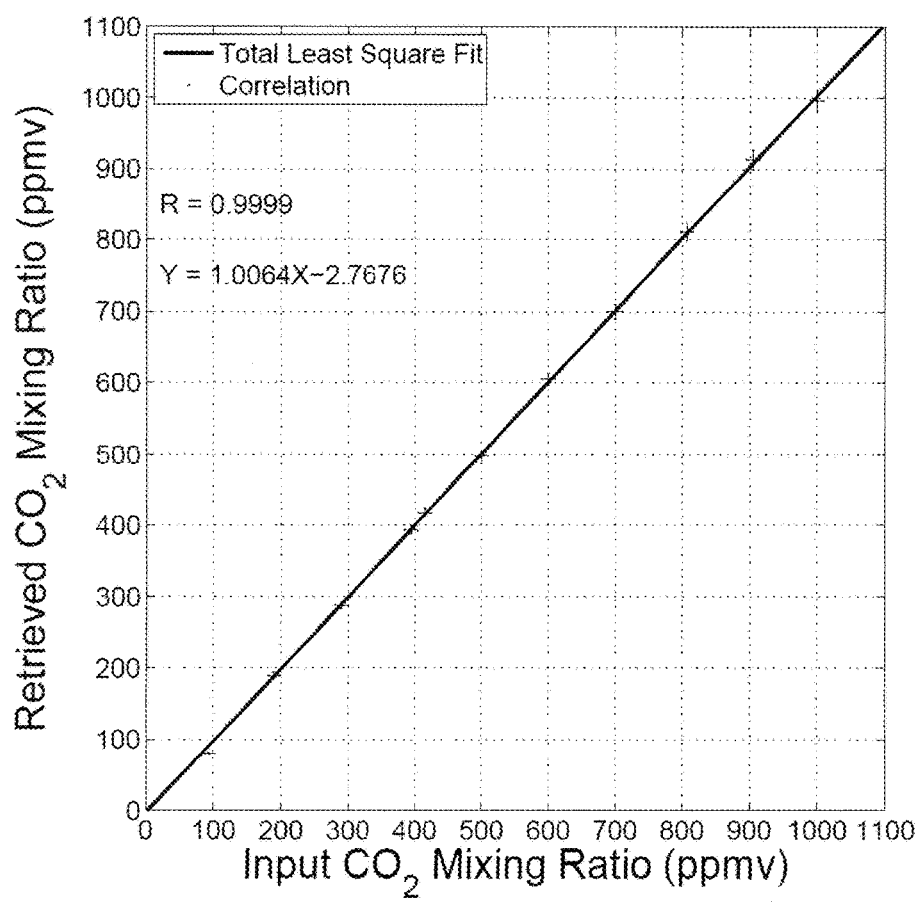
FIG. 7 is a plot showing a validation of the dispersive infrared measurement of $CO_2$ using the device in FIG. 1A.

The dispersive infrared $CO_2$ measurements and retrieval results were validated by a 10 point standard $CO_2$ gas calibration with concentrations ranging from 100 ppmv to 1000 ppmv. With reference to FIG. 7, where is shown the comparison of the $CO_2$ mixing ratios retrieved by the dispersive infrared instrument and the standard concentration. The retrieved $CO_2$ mixing ratio agrees with the input concentration with a Pearson correlation coefficient (R) of 0.9999. The slope of a total least squares regression between the two datasets is 1.01 with an offset of −2.77 ppmv. The offset between the two datasets may result from residual $CO_2$ trace amounts in the zero air of the reference lamp spectrum measurement.

Figure 8:
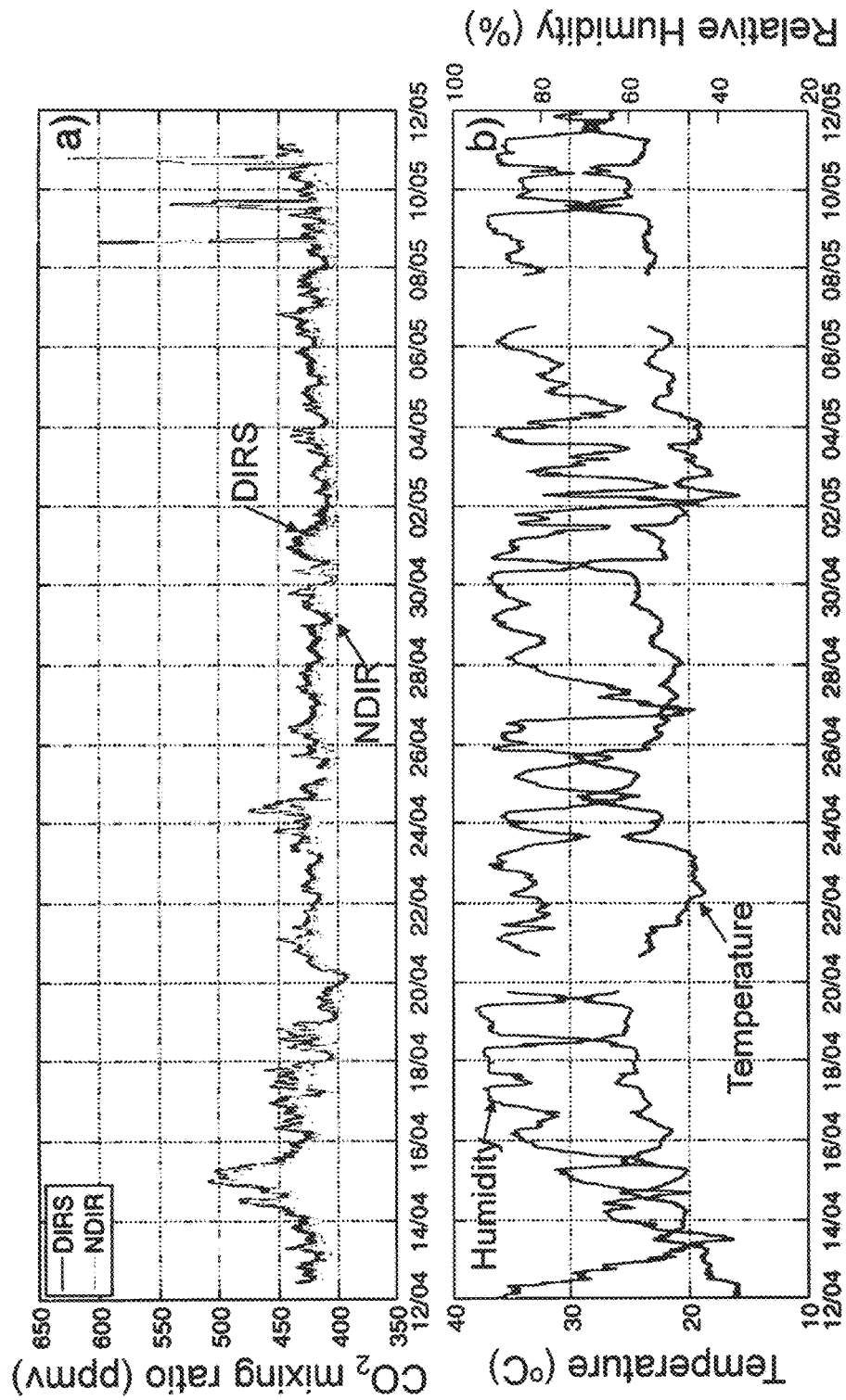
FIG. 8A is a plot showing time series of ambient $CO_2$ measured by the device in FIG. 1A and the an NDIR instrument.
FIG. 8B is a plot showing the temperature and relative humility data recorded.

Referring to FIG. 8, there is shown the time series of the atmospheric $CO_2$ measurements obtained from the dispersive infrared instrument and the Vaisala GMP 343 $CO_2$ analyzer. The reference Vaisala analyzer is a single beam dual wavelength NDIR based $CO_2$ sensor with an accuracy of ±(3 ppmv+1% of the measurement value) as specified by the manufacturer with internal correction of pressure and humidity. The use of reference wavelength compensates the sensor aging and contamination, increasing its stability for long term measurement. The analyzer also went through two point standard gas calibration prior to the experiments. The micrometeorological conditions such as temperature and relative humidity recorded by the weather station at City University of Hong Kong are also shown in FIG. 8 for reference. For DIRS analyzer, the mean measurement error of the $CO_2$ measurement for 1 minute averaged data is about 2.5 ppmv and drops to 0.8 ppmv for the 10 minute average. The data presented in the plot are time averaged data with a 10 minute resolution. Overall, an excellent agreement was demonstrated between the DIRS and reference NDIR $CO_2$ analyzer. Although the DIRS measurement has a different sampling resolution than the reference analyzer, it could successfully retrieve the peaks and troughs during transient events. The mean $CO_2$ mixing ratios measured by the DIRS and the Vaisala $CO_2$ analyzer during the one month measurement were 424.9 ppmv and 420.9 ppmv, respectively, well within the uncertainty of calibration for the reference analyzer.

Figure 9:
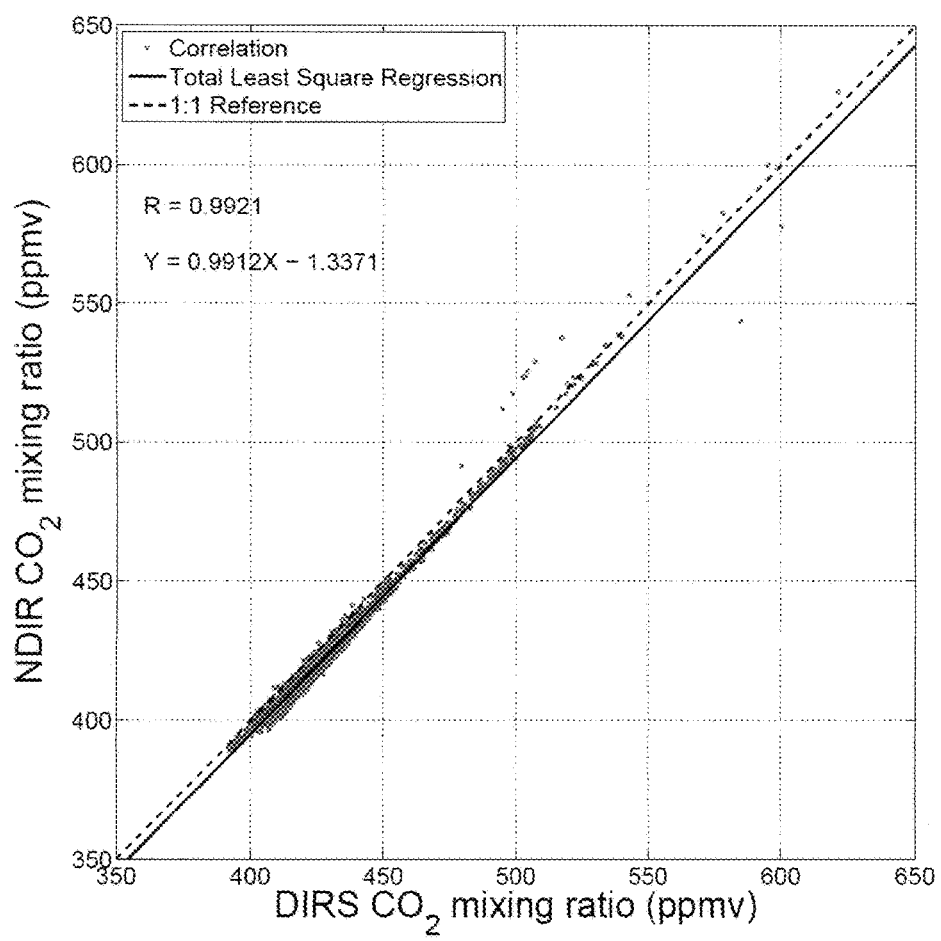
FIG. 9 is a plot showing a correlation between $CO_2$ concentrations measured by the device in FIG. 1A (X-axis) and an NDIR instrument (Y-axis)
Figure 10:
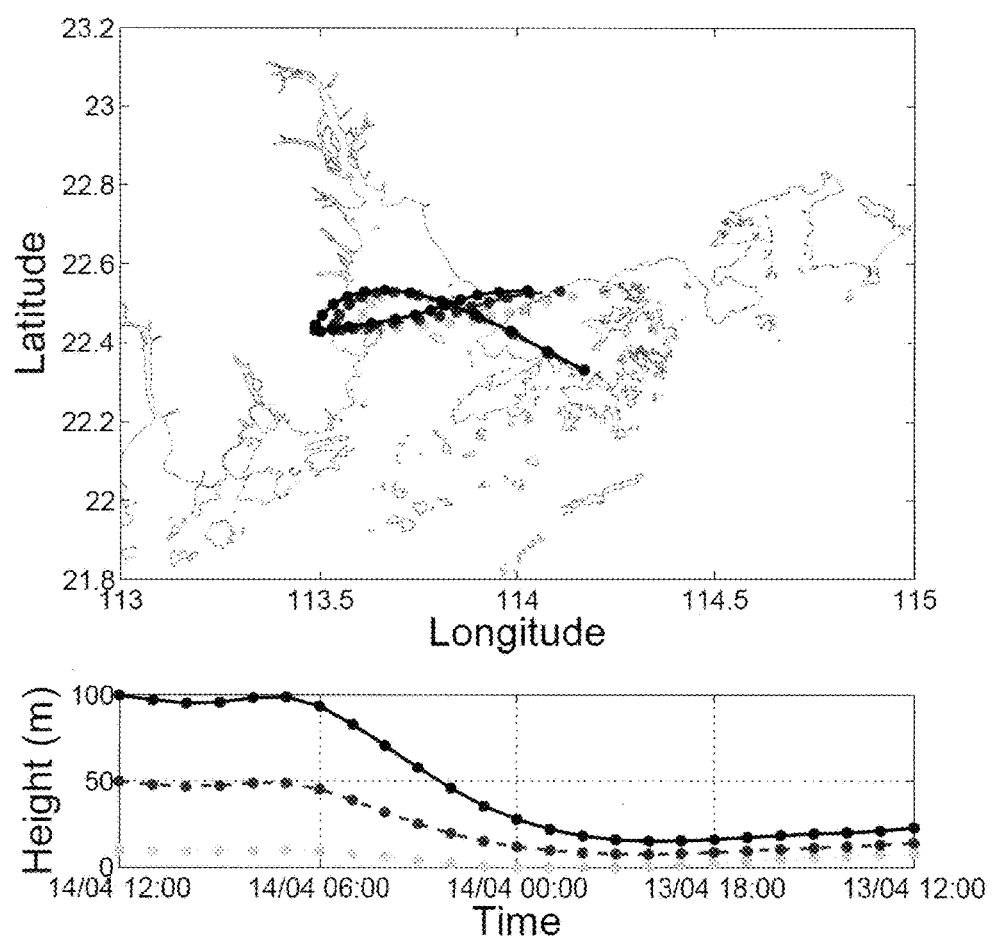
FIG. 10 is a plot showing a 24 hour backward trajectory simulations for the $CO_2$ episode.

Referring to FIG. 9, there is shown the correlation curve of the two datasets with total least square regression. An overall very good agreement was achieved with a Pearson correlation coefficient (R) of 0.9921 and a slope of 0.9912. The offset between the two measurements is 1.34 ppmv. This small offset might result from the uncertainty of the calibration for the reference analyzer.

It is observed that, during the atmospheric $CO_2$ measurements, there was a large $CO_2$ peak on 14 and 15 Apr. 2013. During this period, the atmospheric $CO_2$ levels reached over 500 ppmv and lasted for almost two days. The possible causes of this episode were investigated using the Hybrid Single Particle Lagrangian Integrated Trajectory (HYSPLIT) model. 24 hour backward trajectories, as shown in FIG. 1A0, show that the air mass recirculated in the region which indicates that the observed $CO_2$ episode may result from the accumulation of local emissions. Several sharp peaks were also obtained during the period of 8 to 11 May 2013. The values of those peaks were very high (over 600 ppmv) and only lasted for a short period, which is likely due to local emissions. A sudden increase of traffic in the area of the monitoring station would result in a sharp rise of $CO_2$ levels.

Figure 11:
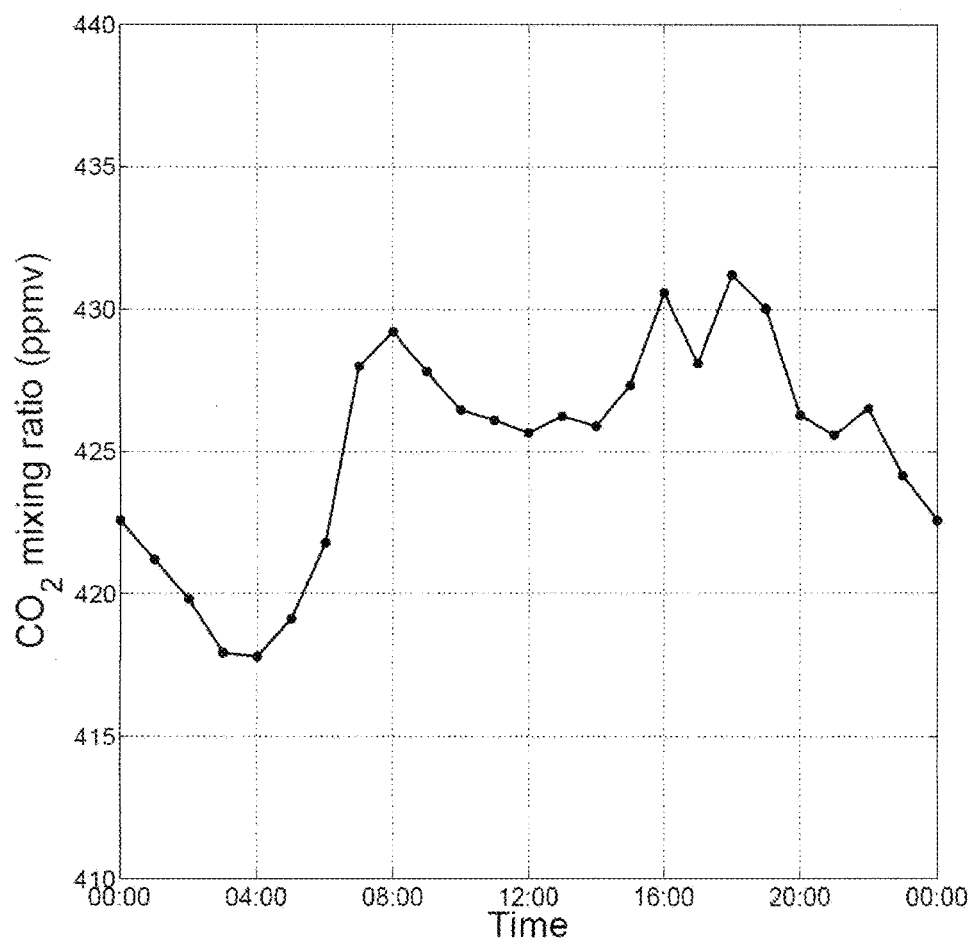
FIG. 11 is a plot showing a mean diurnal cycle of atmospheric $CO_2$ measured by the device of FIG. 1A.

In urban areas, the atmospheric $CO_2$ levels are closely related to anthropogenic emissions. Analyzing the diurnal cycle of atmospheric $CO_2$ can give further information on $CO_2$ sources and sinks. With reference to FIG. 11, there is shown the mean diurnal cycle of atmospheric $CO_2$ measured by the dispersive infrared instrument during a measurement period of one month. The atmospheric $CO_2$ levels show a pronounced diurnal pattern with peak value during the evening rush hours and minimum value in the early morning. In general, the atmospheric $CO_2$ levels reach a minimum in the early morning at around 04:00 (local time), followed by a sharp increase of about 12 ppmv from 05:00 to 09:00 (local time). The $CO_2$ values drop gradually around noon time then increase again and reach the daily maximum at around 18:00 (local time). The bimodal $CO_2$ profile in the diurnal cycle is mainly related to the increase in traffic load during the morning and evening rush hours. Relatively lower traffic emissions during the night probably result in lower observed $CO_2$ levels. Future investigation will involve longer term atmospheric monitoring of $CO_2$ to cover its seasonal variation and better understand their sources and sinks in complex urban terrains.

In an example embodiment, there is provided a device 100 of dispersive infrared spectroscopy (DIRS) based continuous atmospheric measurement of $CO_2$ using a compact Fabry-Pérot interferometer (FPI) sensor 108 in the mid infrared (3900 nm to 5220 nm) wavelength range. The $CO_2$ concentration is determined from the measured optical absorption spectra by fitting it to the $CO_2$ reference spectrum. With the inclusion of reference absorption spectrum of other infrared absorbing gases in the fitting, for example, carbon monoxide (CO) and water vapor ($H_2O$), the $CO_2$ measurement is insensitive to the influence of the varying ambient humidity and absorber concentrations. Preferably, an iterative algorithm may be implemented for the correction of non-linear absorption commonly found in low spectrum resolution instruments. Advantageously, as shown in the simulation results, multiple wavelength measurements considerably reduce measurement error induced by instrument noise are obtained. The modelling study also shows that the iterative retrieval algorithm is sensitive to the instrument resolution function.

Advantageously, the device for detecting a substance, the developed DIRS instrument and retrieval algorithm are featured with high accuracy, moderate cost, compact size and correction capability for water vapor interference. By including reference spectra of other infrared absorbing gases in the algorithm, the method can also determine multiple gas concentrations simultaneously. The use of a MEMS (such as a MEMS as shown in FIG. 1B) for the scanning Fabry-Pérot interferometer greatly reduces the system size and lowers the cost when compared to other systems of equal performance, making it an option for applications of atmospheric $CO_2$ monitoring and indoor air quality measurements.

For example, the method for detecting a gas in an embodiment involves a measurement technique based on the inversion technique on wide gas absorption mid infrared spectra from 3 to 5 μm and the reference spectrum of $CO_2$, $CH_4$, $H_2O$ and other potentially interfering gases to achieve a gas and humidity interference free detection of the greenhouse gases. This facilitates applications such as outdoor, indoor, emission monitoring where water vapor has large concentrations. Advantageously, such method and device will enhance the accuracy and detection sensitivity of greenhouse gases. At the same time, the method and the device will realize calibration-free detection due to the inclusion of reference spectrum.

Figure 1C:
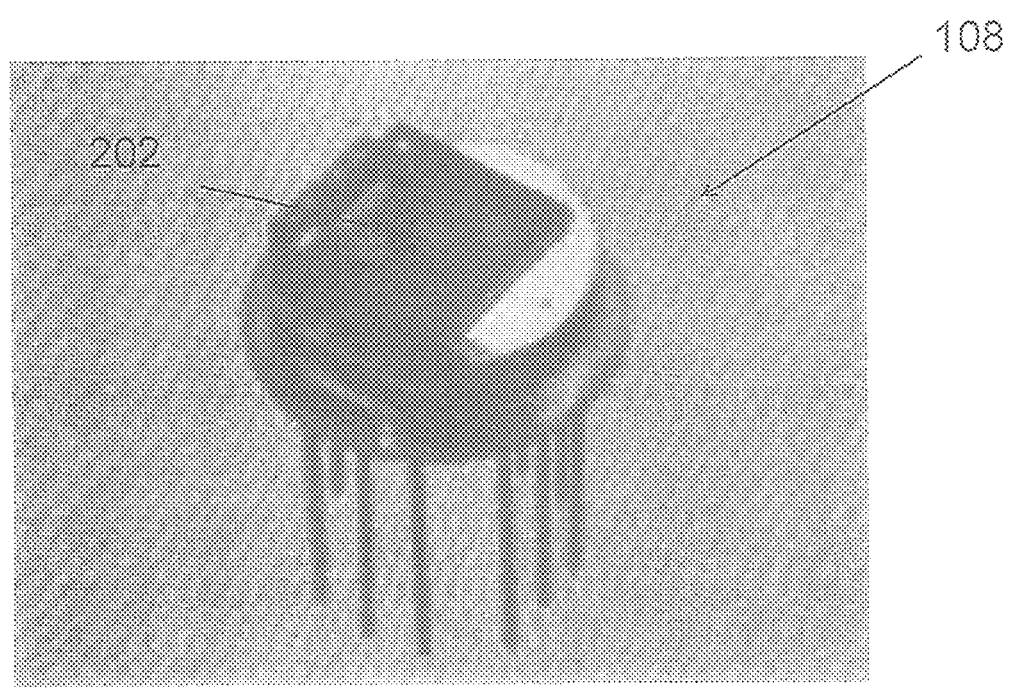
FIG. 1C is an image of an FPI sensor in the device of FIG. 1A.

It is also advantageous in that, such method adopts a miniature tunable infrared filter and a Fabry-Pérot Interferometer (FPI) to realize extremely small size infrared detection with multiple wavelength (more than 50 channels from 4 to 5 μm range with about 70 nm for each channel). For example, an as shown in FIGS. 1B and 1C, the interferometer 108 may have a structure which has a built-in photo detector with two parallel layers of glass 202 separated by a variable distance controlled with certain voltage VC by external power supply. The use of such micro system 200 greatly reduces the size and cost of the device. In some embodiments, an FPI chip 108 has a dimension of less than 1 cm height and 1 cm diameter.

By using the multiple wavelength algorithm, an auto-correction function is arranged to solve the non-linear absorption effect that has been a major problem in traditional NDIR technologies. This is caused by the contradiction between very narrow absorption of greenhouse gas in certain wavelength and the wider range of wavelength detection in NDIR technology. Such problem is solved by multiple wavelength scanning and calculation to derive the mathematical solution. This will result in a wide range detection of the gases without having to perform time consuming calibration.

Without deviating from the spirit of the invention, the device for detecting a gas can be modified to detect greenhouse gases other than $CO_2$, such as $H_2O$, $CH_4$, $N_2O$, $O_3$ or CFCs. In some embodiments, the device can be arranged detect gas other then greenhouse gases, as known by a person skilled in the art.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A device for detecting a substance comprising:
a light source arranged to emit a light signal through a sample cell, wherein the sample cell is arranged to temporally house a sample compound having a portion of the substance; and
an optical processing module arranged to detect the light signal emitted through the sample cell to identify physical attributes of the light signal altered by the sample compound at multiple wavelengths, the light signal is at least partially absorbed by the sample compound in the sample cell;
wherein the physical attributes of the light signal altered by the sample compound are processed by fitting the physical attributes at the multiple wavelengths to a reference absorption spectrum of the substance so as to detect the substance within the sample compound; and
wherein the optical processing module includes a light sensor and a micro-electric-mechanical-system arranged to enable the light sensor to detect the physical attributes of the altered light signal at the multiple wavelengths; and
wherein the optical processing module is further arranged to process the detected physical attributes using an iterative retrieval process so as to correct a non-linear effect of the light signal altered by the sample compound in a dispersive infrared spectroscopy measurement process; the iterative retrieval process includes:
a convolution process of high resolution cross sections with an instrument spectral resolution of the optical processing module; and
a second order polynomial in a fitting process between a measured absorption spectrum and a reference absorption spectrum of the sample compound; wherein the fitting process is carried out using a modified absorption cross section represented by:

$$\sigma_{i,n+1}(\lambda) = \frac{-\ln(\exp(-L \cdot \sigma_{i,n}(\lambda) \cdot c_{i,n}) * F(\lambda'))}{L \cdot c_{i,n}}$$

where L represents a distance that the light signal passes through the sample compound, c represents a concentration of the sample compound, and F represents an instrument function associated with an influence of the instrument on the spectra including the sampling process.

2. A device for detecting a substance in accordance with claim 1, wherein the sample compound includes a gas.

3. A device for detecting a substance in accordance with claim 1, wherein the optical processing comprises a light sensor.

4. A device for detecting a substance in accordance with claim 3, wherein the light sensor includes a pyroelectric sensor.

5. A device for detecting a substance in accordance with claim 4, wherein the light sensor further includes a Fabry-Pérot interferometer.

6. A device for detecting a substance in accordance with claim 5, wherein the pyroelectric sensor is integrated with the Fabry-Pérot interferometer.

7. A device for detecting a substance in accordance with claim 3, wherein the light sensor is a Fabry-Pérot interferometer sensor.

8. A device for detecting a substance in accordance with claim 1, wherein the physical attributes include a signal strength of the light signal at one or more wavelengths emitted by the light source.

9. A device for detecting a substance in accordance with claim 8, wherein the physical attributes include an optical spectrum of the light signal emitted by the light source.

10. A device for detecting a substance in accordance with claim 9, wherein the light source is a broad band infrared light source.

11. A device for detecting a substance in accordance with claim 10, wherein the light signal is in a range of wavelengths between 3 μm to 5 μm.

12. A device for detecting a substance in accordance with claim 1, wherein the optical processing module further comprises a photo detector and two layers of glass separated by a variable distance controlled by a variable electrical signal.

13. A device for detecting a substance in accordance with claim 2, wherein the sample cell is a gas cell arranged to connect with a gas flow system for flowing the gas into and out of the gas cell.

14. A device for detecting a substance in accordance with claim 13, wherein the air flow system comprises an HEPA filter at an inlet of the gas cell for blocking aerosol from entering the gas cell.

15. A device for detecting a substance in accordance with claim 1, the substance includes a greenhouse gas.

16. A device for detecting a substance in accordance with claim 1, the substance includes at least one of carbon dioxide, methane, nitrous oxide or water.

17. A method for detecting a substance comprising the steps of:
temporally housing a sample compound having a portion of the substance;
emitting a light signal through the sample compound such that the light signal is at least partially absorbed by the sample compound;
manipulating with a micro-electro-mechanical-system so as to enable a detection of the light signal at multiple wavelengths;
detecting the light signal at the multiple wavelengths emitted through the sample-compound; and
processing the detected light signal;
wherein physical attributes of the light signal altered by the sample compound is identified and processed by fitting the physical attributes at the multiple wavelengths to a reference absorption spectrum of the substance so as to detect the substance within the sample compound; and
wherein the identified physical attributes are further processed using an iterative retrieval process such that a non-linear effect of the light signal altered by the sample compound in a dispersive infrared spectroscopy measurement process is corrected; the iterative retrieval process includes:
a convolution process of high resolution cross sections with an instrument spectral resolution of an optical processing module arranged to emit and to detect the light signal; and
a second order polynomial in a fitting process between a measured absorption spectrum and a reference absorption spectrum of the sample compound; wherein the fitting process is carried out using a modified absorption cross section represented by:

$$\sigma_{i,n+1}(\lambda) = \frac{-\ln(\exp(-L \cdot \sigma_{i,n}(\lambda) \cdot c_{i,n}) * F(\lambda'))}{L \cdot c_{i,n}}$$

where L represents a distance that the light signal passes through the sample compound, c represents a concentration of the sample compound, and F represents an instrument function associated with an influence of the instrument on the spectra including the sampling process.

18. A method for detecting a substance in accordance with claim 17, wherein the light signal is detected by a Fabry-Pérot interferometer sensor.

19. A method for detecting a substance in accordance with claim 17, wherein the physical attribute includes a signal strength of the light signal emitted at one or more wavelengths.

20. A method for detecting a substance in accordance with claim 19, wherein the physical attribute includes an optical spectrum of the emitted light signal.

21. A method for detecting a substance in accordance with claim 17, wherein the light source is emitted by a broad band infrared light source.

22. A method for detecting a substance in accordance with claim 17, wherein the sample compound includes a gas, and is temporally housed in a gas cell arranged to connect with an air flow system for flowing the gas into and out of the gas cell.

23. A method for detecting a substance in accordance with claim 17, the substance includes a greenhouse gas.

* * * * *